United States Patent
Goldberg et al.

(10) Patent No.: US 12,102,429 B2
(45) Date of Patent: Oct. 1, 2024

(54) PERSONALIZED CALIBRATION FOR GLUCOSE SENSING

(71) Applicant: Laxmi Therapeutic Devices, Inc., Goleta, CA (US)

(72) Inventors: Jason Goldberg, Oakland, CA (US); Sarah Clabeaux, Ventura, CA (US); Reghu Kunnath Rajan, Whittier, CA (US); William Van Antwerp, Santa Clarita, CA (US)

(73) Assignee: LAXMI THERAPEUTIC DEVICES, INC., Goleta, CA (US)

( * ) Notice: Subject to any disclaimer, the term of this patent is extended or adjusted under 35 U.S.C. 154(b) by 0 days.

(21) Appl. No.: 18/093,799

(22) Filed: Jan. 5, 2023

(65) Prior Publication Data
US 2023/0218204 A1 Jul. 13, 2023

Related U.S. Application Data

(60) Provisional application No. 63/297,581, filed on Jan. 7, 2022.

(51) Int. Cl.
*A61B 5/145* (2006.01)
*A61B 5/00* (2006.01)
*A61B 5/1495* (2006.01)

(52) U.S. Cl.
CPC ........ *A61B 5/14532* (2013.01); *A61B 5/1495* (2013.01); *A61B 2560/0238* (2013.01)

(58) Field of Classification Search
CPC .............. A61B 5/14532; A61B 5/1495; A61B 2560/0238
See application file for complete search history.

(56) References Cited

U.S. PATENT DOCUMENTS

| | | |
|---|---|---|
| 2010/0185175 A1 | 7/2010 | Kamen et al. |
| 2011/0218489 A1 | 9/2011 | Mastrototaro et al. |

(Continued)

OTHER PUBLICATIONS

Guerra S, Facchinetti A, Sparacino G, Nicolao GD, Cobelli C. Enhancing the accuracy of subcutaneous glucose sensors: a real-time deconvolution-based approach. IEEE Trans Biomed Eng. Jun. 2012;59(6):1658-69. doi: 10.1109/TBME.2012.2191782. Epub Mar. 23, 2012. PMID: 22481799. (Year: 2012).*

(Continued)

*Primary Examiner* — Charles A Marmor, II
*Assistant Examiner* — Meghan R Kumar
(74) *Attorney, Agent, or Firm* — Lewis Roca Rothgerber Christie LLP (57) ABSTRACT

A system and method for personalized calibration for glucose sensing. In some embodiments, the method includes obtaining a plurality of first glucose measurements from a subject, at a plurality of first sampling times during a time interval, using a first glucose sensor; obtaining a plurality of second glucose measurements from the subject, at a plurality of second sampling times during the time interval, using a second glucose sensor; and estimating a first in-vivo calibration parameter for the first glucose sensor and the second glucose sensor, based on the first glucose measurements and the second glucose measurements, wherein a first in-vivo time-constant, relating blood glucose to an output of the first glucose sensor, is different from a second in-vivo time-constant, relating blood glucose to an output of the second glucose sensor.

13 Claims, 7 Drawing Sheets

(56) References Cited

U.S. PATENT DOCUMENTS

| | | | |
|---|---|---|---|
| 2015/0282744 A1 | 10/2015 | Roy et al. | |
| 2019/0175079 A1 | 6/2019 | Nishida et al. | |
| 2020/0352479 A1* | 11/2020 | Rebec | A61B 5/1495 |
| 2020/0352480 A1* | 11/2020 | Lucisano | A61B 5/14503 |
| 2020/0383643 A1* | 12/2020 | Singh | A61B 5/14532 |

OTHER PUBLICATIONS

International Search Report and Written Opinion for Application No. PCT/US23/10249, mailed Mar. 29, 2023, 12 pages.

* cited by examiner

PERSONALIZED CALIBRATION FOR GLUCOSE SENSING

CROSS-REFERENCE TO RELATED APPLICATION(S)

The present application claims priority to and the benefit of U.S. Provisional Application No. 63/297,581, filed Jan. 7, 2022, entitled "PERSONALIZED CALIBRATION FOR GLUCOSE SENSING", the entire content of which is incorporated herein by reference.

FIELD

One or more aspects of embodiments according to the present disclosure relate to glucose monitoring, and more particularly to a system and method for personalized calibration for glucose sensing.

BACKGROUND

Glucose measurements may be made in the blood of a subject, or in the interstitial fluid of the subject. The interstitial glucose concentration may be related to the blood glucose concentration by various mechanisms, including diffusion.

It is with respect to this general technical environment that aspects of the present disclosure are related.

SUMMARY

According to an embodiment of the present disclosure, there is provided a method, including: obtaining a plurality of first glucose measurements from a subject, at a plurality of first sampling times during a time interval, using a first glucose sensor; obtaining a plurality of second glucose measurements from the subject, at a plurality of second sampling times during the time interval, using a second glucose sensor; and estimating a first in-vivo calibration parameter for the first glucose sensor and the second glucose sensor, based on the first glucose measurements and the second glucose measurements, wherein a first in-vivo time-constant, relating blood glucose to an output of the first glucose sensor, is different from a second in-vivo time-constant, relating blood glucose to an output of the second glucose sensor.

In some embodiments the first in-vivo calibration parameter is the first in-vivo time-constant.

In some embodiments the method further includes estimating a blood glucose level based on: a glucose measurement from the first glucose sensor; and the estimated first in-vivo time-constant.

In some embodiments the method further includes estimating the second in-vivo time-constant.

In some embodiments the method further includes estimating a blood glucose level based on: a glucose measurement from the first glucose sensor; a glucose measurement from the second glucose sensor; the estimated first in-vivo time-constant; and the estimated second in-vivo time-constant.

In some embodiments: the estimating includes selecting a first time-constant and a second time-constant for which a measure of the difference between a first signal history and a second signal history is minimized; and each of the first signal history and the second signal history is based on the first glucose measurements or the second glucose measurements or a first hypothesized time-constant or a second hypothesized time-constant.

In some embodiments the method further includes calculating a plurality of first signal histories including the first signal history, the calculating of each of the first signal histories including deconvolving the first glucose measurements with a respective deconvolver of a set of deconvolvers each tuned to a respective one of a plurality of hypothesized time-constants including the first hypothesized time-constant.

In some embodiments: the measure of the difference between the first signal history and the second signal history is a measure of the difference between an estimated blood glucose history based on the first glucose measurements and an estimated blood glucose history based on the second glucose measurements; and the measure of the difference between the estimated blood glucose history based on the first glucose measurements and the estimated blood glucose history based on the second glucose measurements is selected from the group consisting of a root mean square error, a mean squared error, an average difference, an average relative difference, and the median of average differences.

In some embodiments, the measure of the difference between the estimated blood glucose history based on the first glucose measurements and the estimated blood glucose history based on the second glucose measurements is a root mean square error.

In some embodiments the method includes estimating the difference between the first time-constant and the second time-constant.

In some embodiments: the first glucose sensor is in a deep subcutaneous space of the subject; and the second glucose sensor is in a shallow dermis of the subject.

According to an embodiment of the present disclosure, there is provided a system, including: a processing circuit; and memory, operatively connected to the processing circuit and storing instructions that, when executed by the processing circuit, cause the system to perform a method, the method including: obtaining a plurality of first glucose measurements from a subject, at a plurality of first sampling times during a time interval, using a first glucose sensor; obtaining a plurality of second glucose measurements from the subject, at a plurality of second sampling times during the time interval, using a second glucose sensor; and estimating a first in-vivo calibration parameter for the first glucose sensor and the second glucose sensor, based on the first glucose measurements and the second glucose measurements, wherein a first in-vivo time-constant, relating blood glucose to an output of the first glucose sensor, is different from a second in-vivo time-constant, relating blood glucose to an output of the second glucose sensor.

In some embodiments, the first in-vivo calibration parameter is the first in-vivo time-constant.

In some embodiments, the method further includes estimating a blood glucose level based on: a glucose measurement from the first glucose sensor; and the estimated first in-vivo time-constant.

In some embodiments, the method further includes estimating the second in-vivo time-constant.

In some embodiments, the method further includes estimating a blood glucose level based on: a glucose measurement from the first glucose sensor; a glucose measurement from the second glucose sensor; the estimated first in-vivo time-constant; and the estimated second in-vivo time-constant.

In some embodiments: the estimating includes selecting a first time-constant and a second time-constant for which a measure of the difference between a first signal history and a second signal history is minimized; and each of the first signal history and the second signal history is based on the first glucose measurements or the second glucose measurements or a first hypothesized time-constant or a second hypothesized time-constant.

In some embodiments: the measure of the difference between the first signal history and the second signal history is a measure of the difference between an estimated blood glucose history based on the first glucose measurements and an estimated blood glucose history based on the second glucose measurements; and the measure of the difference between the estimated blood glucose history based on the first glucose measurements and the estimated blood glucose history based on the second glucose measurements is selected from the group consisting of a root mean square error, a mean squared error, an average difference, an average relative difference, and the median of average differences.

In some embodiments, the method further includes estimating the difference between the first time-constant and the second time-constant.

In some embodiments, the obtaining of the first glucose measurements includes obtaining the first glucose measurements using an electro-chemical sensor of a continuous glucose monitor.

BRIEF DESCRIPTION OF THE DRAWINGS

These and other features and advantages of the present disclosure will be appreciated and understood with reference to the specification, claims, and appended drawings wherein:

DETAILED DESCRIPTION

The detailed description set forth below in connection with the appended drawings is intended as a description of exemplary embodiments of a personalized calibration method for glucose sensing provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Factory calibrated glucose sensors may allow patients (or "subjects") to successfully manage their diabetes without the pain and annoyance of finger sticks. Four major parameters may be relevant to the feasibility of factory calibration: (i) repeatable manufacturing at least on a batch level with limited variability (e.g., variability <5%) for a given batch, (ii) a repeatable in-vitro to in-vivo sensitivity relationship (iii) repeatable and well understood in-vivo (and in-vitro) stability, particularly the stability of the sensitivity, and (iv) a well understood relationship between blood glucose and tissue glucose (e.g., interstitial glucose, the glucose level in the interstitial fluid) for the entire population of expected patients.

Once these four parameters have been obtained, a factory calibration can be contemplated. The fourth parameter (a well understood relationship between blood and tissue glucose) may be difficult to obtain; significant clinical experience may be required to obtain enough data to establish a population-based estimate. There may be significant patient to patient variability in the time delays between the blood and the tissue glucose. For example, the relationship between fluctuations in the blood glucose, and fluctuations in the interstitial glucose level may be modeled as a low-pass filter characterized by a time constant, which may vary from patient to patient (and which may depend on other factors, such as the implantation depth of a sensor). This variability may cause, e.g., a potential 5% effect on mean absolute relative difference (MARD) (discussed in further detail below) for a given patient.

In some embodiments, a calibration approach may be employed to unambiguously determine the correct time-constants for individual patients yielding a true personalized calibration for any patient, once the first three assumptions have been satisfied. As discussed in further detail below, this approach may involve (i) implanting two interstitial glucose sensors in a patient (e.g., at different depths), so that the two respective time-constants relating blood glucose to interstitial glucose are different, and (ii) inferring both of the time-constants from the histories of sensed interstitial glucose levels from the two sensors.

Figure 1:
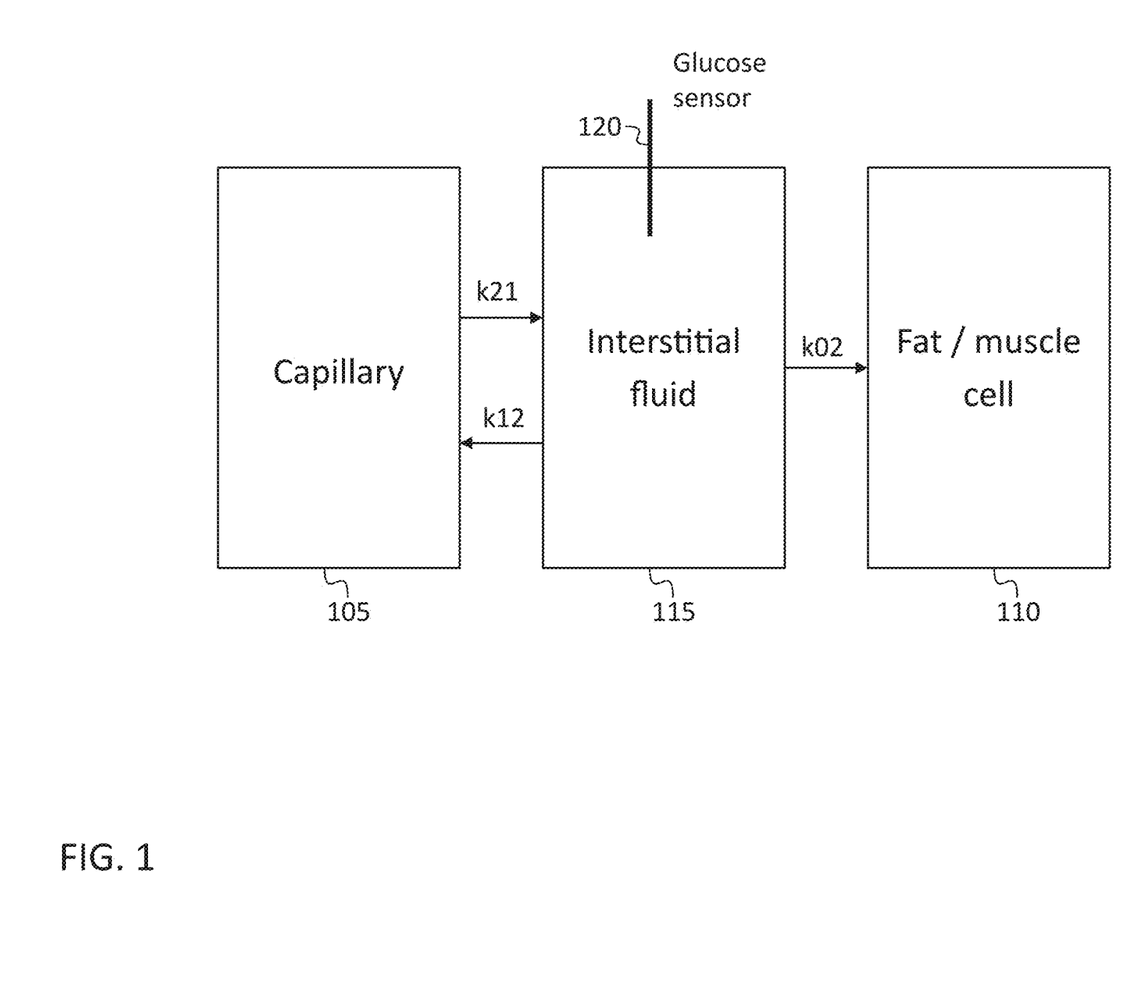
FIG. 1 is a schematic drawing of a two-compartment model, according to an embodiment of the present disclosure.

A two-compartment model may be used to model the relationship between blood glucose and interstitial glucose. The model is shown graphically in FIG. 1, from a physiological standpoint. In FIG. 1, glucose diffuses between a capillary 105, a fat or muscle cell 110, and interstitial fluid 115, where it is sensed by a glucose sensor 120. The response of the interstitial glucose to a hypothetical step in the blood glucose may be that of a low-pass filter. The two-compartment model is one example of a model upon which some embodiments may be based; in other embodiments a different model (e.g., a model based on a second order system, or a nonlinear system) may be employed.

Fundamentally, the interstitial glucose may be measured (in the interstitial fluid surrounding the tissue) and then a model may be used to reconstruct what the blood glucose would be for a given interstitial glucose measurement and for a history of interstitial glucose values (as discussed in further detail below). For any sensor there is, according to the two-compartment model, a single diffusion time-constant $\tau$ that describes the relationship between blood glucose and interstitial glucose. This parameter may however be subject dependent; population-based estimates may be used, but these may result in errors in prediction. As discussed in further detail below, however, it may be possible to use two sensors placed in different tissue locations with significantly different τ values, and to infer both τ values with reasonable certainty, to arrive at a true individualized calibration.

For example, a first sensor may be placed in the deep subcutaneous (SQ) tissue (lipid) where τ may be 12-15 minutes and a second sensor may be placed in the shallow dermis where τ is considerably smaller. The sensors may have (i) different, and known, sensor calibration parameters (e.g., sensitivity and baseline), or (ii) unknown and similar sensitivity characteristics, or (iii) known and similar (although methods disclosed herein may be effective even if the sensor calibration parameters are not both known and similar). Further, the sensors may have known filtering characteristics (which may be due in part to their mass transfer properties), or the filtering characteristics may correspond to time-constants that are significantly shorter than τ. For example, as shown below, under certain assumptions, if the blood glucose is estimated, as a function of time (i) for the first sensor based on a first hypothesized time-constant $\tilde{\tau}_0$ and (ii) for the second sensor based on a second hypothesized time-constant $\tilde{\tau}_1$, the first blood glucose estimate will equal the second blood glucose estimate, over time, if and only if each of the hypothesized time-constants is equal to the corresponding true time-constant. This is illustrated in FIG. 2A, which shows the root mean squared error (RMSE), where the error is defined as the difference between (i) the estimated blood glucose history based on the measurements of the first sensor (with hypothesized time-constant ("Tau1") on the vertical axis), and (ii) the estimated blood glucose history based on the measurements of the second sensor (with hypothesized time-constant ("Tau2") on the horizontal axis).

Figure 2A:
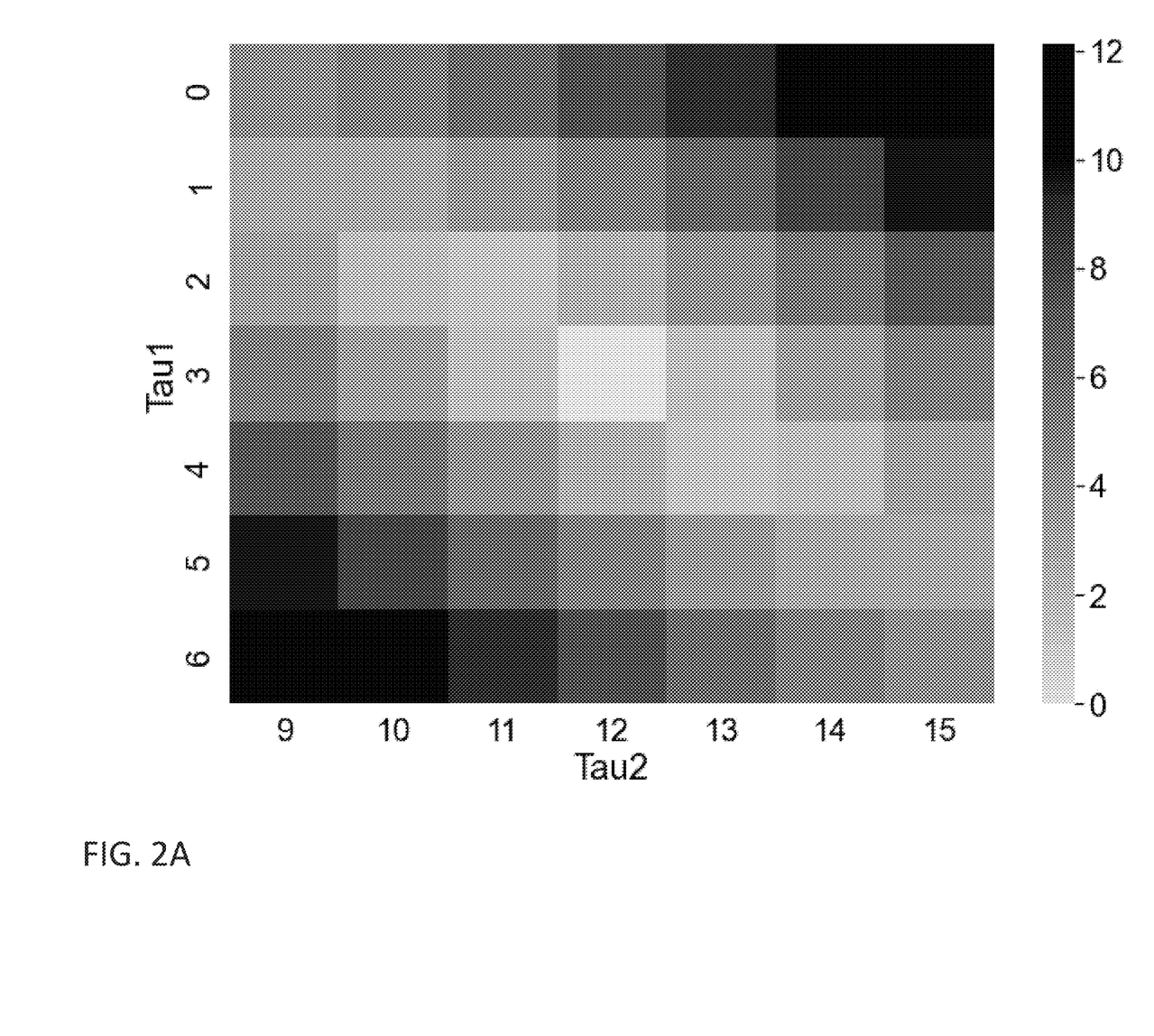
FIG. 2A is a graph of root mean squared error, according to an embodiment of the present disclosure.
Figure 2B:
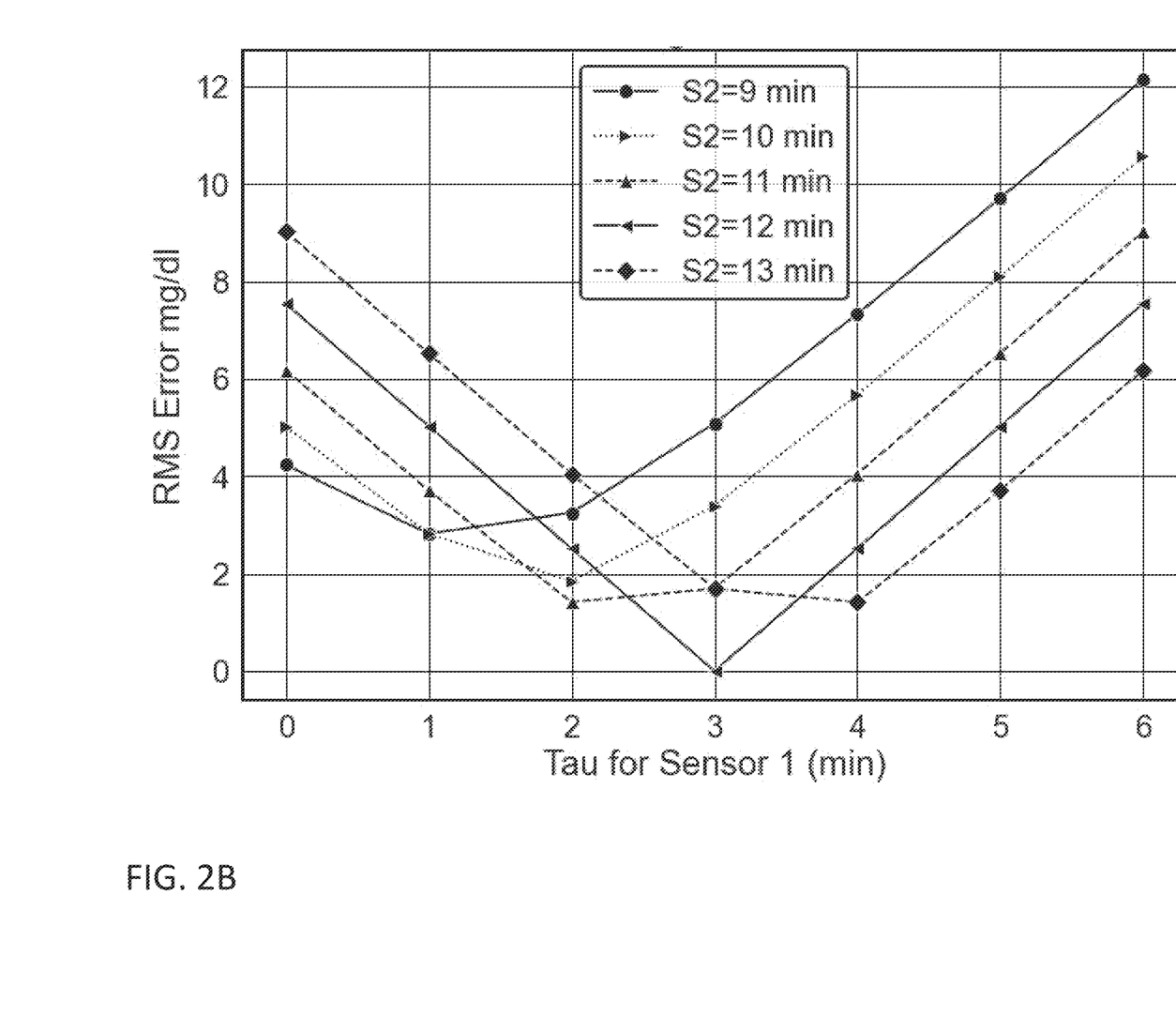
FIG. 2B is a graph of root mean squared error, according to an embodiment of the present disclosure.

In FIG. 2A, the time-constant $\tau_0$ of the first sensor is 3 minutes and the time-constant $\tau_1$ of the second sensor is 12 minutes. FIG. 2B shows the same data, i.e., the RMSE, plotted, as a function of $\tilde{\tau}_0$ ("Tau for Sensor 1"), as four curves (one each for $\tilde{\tau}_1$=9, 10, 11, and 12 minutes ($\tilde{\tau}_1$ being written as "S2" in the legend); the curves for $\tilde{\tau}_1$=15, 14, and 13 would, if plotted, fall on top of the curves for $\tilde{\tau}_1$=9, 10, and 11, respectively). When both the $\tilde{\tau}_0$ and $\tilde{\tau}_1$ values are correct, the RMSE is 0 mg/dl.

In practice, for calibration, two or more sensors may be placed into the subject. For example, one sensor may be placed in the deep subcutaneous space (e.g., between 4.0 mm and 10.0 mm deep) where the expected τ value is 9-15 minutes, and a second sensor may be placed in the shallow dermis (e.g., between 0.5 and 2.0 mm deep) where the expected τ value is 0-6 minutes. During the course of the wear, sensor signals (Isig) may be recorded and comparator data (e.g., finger-stick blood glucose measurements) may be acquired. The data may be analyzed using a parametric model that fits sensor measurements to comparator data by adjusting estimates of in-vivo sensor characteristics (e.g., sensitivity, background current, and time-constant) for each of the sensors. The optimal values of $\tilde{\tau}_0$ and $\tilde{\tau}_1$ may be obtained from this analysis, yielding an individualized calibration for both sensors.

The following section elaborates on methods that may be used to perform a calibration of two glucose sensors having different time-constants (e.g., as a result of being implanted at different depths in a patient). While an electro-chemical sensor used in a continuous glucose monitor (CGM) produces an output current related to interstitial glucose (IG), direct knowledge of blood glucose (BG) may be assumed in a glycemic control strategy. Interstitial glucose may depend on blood glucose through a diffusion relationship. As mentioned above, one description for such BG-IG kinetics, which may be referred to as the two-compartment model, is under certain conditions dependent on a single diffusion time-constant parameter which may vary from subject to subject.

In practice, the diffusion parameter may be inferred from the continuous glucose monitor's electro-chemical sensor (which may produce an electric current that depends on interstitial glucose) using comparator data (e.g., blood glucose data from another source such as finger stick data). Such a sensor may have an imprecisely known sensitivity and baseline. For system modeling problems, significant uncertainty in the sensor parameters may compromise a system's ability to estimate the diffusion parameter. To solve this problem, joint estimation of the diffusion parameter with sensor sensitivity and baseline modeling parameters may be employed. Analogously, for online calibration in field-use settings, a limited number of blood glucose finger-stick measurements may be used to adjust both the diffusion and sensor parameters to improve blood glucose estimation accuracy.

In some embodiments, factory calibration techniques may significantly reduce uncertainty in sensor sensitivity and baseline parameters without the need for finger-sticks. However, in the absence of such data (e.g., finger-stick measurements), the problem of unknown, subject-dependent diffusion may limit the accuracy of the continuous glucose monitor.

As such, some embodiments include a method to estimate the blood glucose-to-interstitial glucose diffusion parameters associated with two or more sensors without the need for finger-stick references. The technique can be generalized to uncalibrated sensors where sensitivity and baseline are unknown. In addition, an associated deconvolution method may be used.

In the two-compartment model, blood glucose is related to interstitial glucose by:

$$\tau \frac{d}{dt} g_i(t) = -g_i(t) + g_b(t) \quad (1)$$

$$\tau \geq 0$$

where $g_b(t)$ and $g_i(t)$ are instantaneous blood glucose and interstitial glucose at time t, and τ is the diffusion time-constant (which varies from person to person and may be less than twenty minutes). Glucose uptake from cells surrounding the sensor probe may be negligible. An approximate, discrete-time form of this relationship may be:

$$\frac{d}{dt} g_i(t) \approx \frac{g_i[k] - g_i[k-1]}{T_s} \quad (2)$$

where $T_s$ is the sample interval. This implies:

$$g_i[k] \approx a g_i[k-1] + (1-a) g_b[k] \quad (3)$$

$$a = \frac{\tau}{\tau + T_s}$$

where $T_s$ may be chosen such that $T_s \ll \tau$.

The difference equation (Equation 3) is a low-pass linear filtering operation which may be represented equivalently in terms of its z-domain transfer function:

$$H(z) = \sum_{m=-\infty}^{\infty} h[m]z^{-m} = \frac{G_i(z)}{G_b(z)} = \frac{1-a}{1-az^{-1}} \quad (4)$$

where the discrete-time system impulse response is:

$$h[m] = \begin{cases} (1-a)a^m & m \geq 0 \\ 0 & m < 0 \end{cases} \quad (5)$$

The impulse response can be used in a discrete-time convolution sum to yield an alternate but equivalent relationship between blood glucose and interstitial glucose:

$$g_i[k] = \sum_{m=0}^{\infty} h[m]g_b[k-m]. \quad (6)$$

A discrete-time model for sensor current as a function of interstitial glucose at discrete-time sample index k may be constructed as follows:

$$I[k] = \alpha[k]g_i[k] + \beta[k] + n[k] \quad (7)$$

where $I[k]$ is the sensor current, $\alpha[k]$ is sensitivity, $g_i[k]$ is interstitial glucose, $\beta[k]$ is background current, and $n[k]$ is additive sensor noise, all at time $kT_s$. The sensor is modeled as responding instantaneously to changes in interstitial glucose, so that the time-constant $\tau$ relating interstitial glucose to blood glucose is also the time-constant relating blood glucose to the output of the sensor.

Figure 3A:
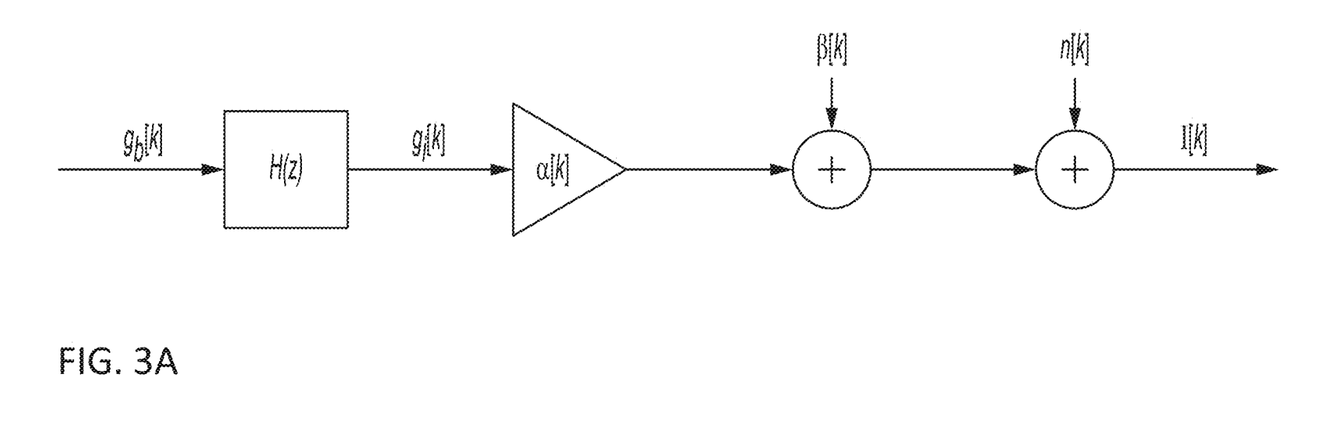
FIG. 3A is a system diagram, according to an embodiment of the present disclosure.

Cascading the diffusion model with the sensor current model gives rise to the end-to-end system diagram shown in FIG. 3A.

In a situation in which perfect knowledge of the sensitivity and background current profiles is available, interstitial glucose may be estimated as:

$$\hat{g}_i[k] = \frac{I[k] - \beta[k]}{\alpha[k]} = \underbrace{g_i[k]}_{desired} + \underbrace{v[k]}_{error} \quad (8)$$

$$v[k] = \frac{n[k]}{\alpha[k]},$$

where, as shown, $g_i[k]$ is the desired signal, and $v[k]$ is the error. As used herein, a hat or caret ("^") denotes an estimate.

Figure 3B:
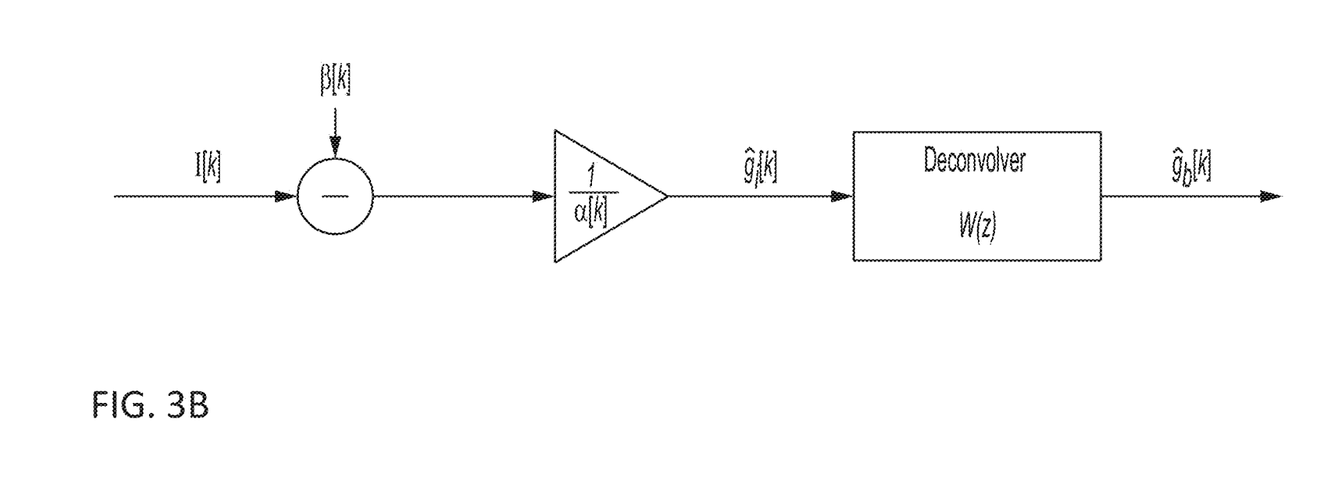
FIG. 3B is a block diagram of a system including a deconvolver, according to an embodiment of the present disclosure.

A subsequent deconvolution stage may be used to estimate blood glucose from $\hat{g}_i[k]$, as shown in FIG. 3B.

In the following, attention is restricted to deconvolvers implemented as length M finite impulse response (FIR) filters with transfer function:

$$W(z) = \sum_{k=0}^{M-1} w[k]z^{-k} \quad (9)$$

In the time domain, the linear filtering operation may be expressed as:

$$\hat{g}_b[k] = \sum_{m=0}^{M-1} w[m]\hat{g}_i[k-m] \quad (10)$$

which is a weighted sum of delayed interstitial glucose estimates.

This approach may be generalized to a scenario with multiple sensors, e.g., a scenario in which multiple (e.g., two or more) sensors are worn simultaneously by a subject. The sensor needles are inserted at different depths under the skin. There may be a direct relationship between sensor needle depth and diffusion time-constant. As such, it is assumed in the analysis that follows that the diffusion time-constants are different.

As a specific example, two sensors may be implanted at different depths. Associated with the shallow sensor is a diffusion time-constant $\tau_0$, while diffusion at the deeper sensor is characterized by time-constant $\tau_1 > \tau_0$. The two time-constants satisfy:

$$\tau_m \in \mathcal{T}_m = [\check{T}_m, \check{T}_m + \Delta_m], \Delta_m > 0, m \in \{0,1\} \quad (11)$$

such that $\mathcal{T}_0 \# \mathcal{T}_1 = \emptyset$ where $\emptyset$ is the empty set. For example, the first sensor may be implanted at a depth of between 0.5 mm and 2.0 mm; associated with this range of implantation depths and patient-to-patient variability may be a set of time-constants $\mathcal{T}_0$ (between 0 minutes and 6 minutes). Similarly, the second sensor may be implanted at a depth of between 4.0 mm and 10.0 mm, and associated with this range of implantation depths and patient-to-patient variability may be a set of time-constants $\mathcal{T}_1$ (between 9 minutes and 15 minutes).

The problem of diffusion parameter estimation for calibrated sensors may be formulated as the problem of estimating the diffusion time-constants $\tau_0$ and $\tau_1$, given noisy interstitial glucose estimates obtained from each sensor over a set of K contiguous samples:

$$g_{i,m}[k], m \in \{0,1\} k \in \mathcal{K} = \{0,1,\ldots,K-1\}. \quad (12)$$

The problem of diffusion parameter estimation for uncalibrated sensors may be formulated as the problem of estimating the diffusion time-constants $\tau_0$ and $\tau_1$, given noisy current measurements from the two sensors over a set of K contiguous samples:

$$I_m[k], m \in \{0,1\} k \in \mathcal{K} \quad (13)$$

and assuming that K is small enough that the gain and baseline are essentially constant over the K sample observation interval:

$$\alpha_m[k] \approx \alpha_m, \beta_m[k] \approx \beta_m, m \in \{0,1\}, \forall k \in \mathcal{K} \quad (14)$$

The problem of deconvolution may be formulated as the problem of estimating blood glucose if the sensors are calibrated and the diffusion time-constants have been estimated.

The following section presents a theorem and a conjecture relating to multi-sensor diffusion parameters. First, it may be observed that for calibrated sensors, under the assumption of noise-free interstitial glucose measurements:

$$\hat{g}_{i,m}[k] = g_{i,m}[k], \quad (15)$$

if the time-constants were known, simple high-pass deconvolvers tuned to the appropriate time-constant would enable perfect blood glucose recovery:

$$\hat{g}_{b,m}[k] = g_b[k] \quad (16)$$

The transfer functions of the deconvolvers would be:

$$W_m(z) = \frac{1}{H_m(z)} = \frac{1 - a_m z^{-1}}{1 - a_m} \quad (17)$$

$$a_m = \frac{\tau_m}{\tau_m + T_s}$$

such that the cascading of the diffusion low-pass filter and the deconvolving high-pass filter would yield a perfect pass-through system:

$$H_m(z)W_m(z) = 1. \quad (18)$$

This means that the deconvolver outputs would be identical to one another and would correspond exactly to the original blood glucose sequence.

The following theorem (which may be referred to as the identifiability theorem) states that the outputs of two deconvolvers tuned to hypothesized time-constants $\tilde{\tau}_m \in \mathcal{T}_{tm}$, having the following transfer functions:

$$\tilde{W}_m(z) = \frac{1 - \tilde{a}_m z^{-1}}{1 - \tilde{a}_m} \quad (19)$$

$$\tilde{a}_m = \frac{\tilde{\tau}_m}{\tilde{\tau}_m + T_s}$$

will equal one another if and only if the hypothesized time-constants are correct, leading to perfect blood glucose recovery. The identifiability theorem may be written:

For hypothesized time-constants $\tilde{\tau} \in \mathcal{T}_{tm}$, $$H_0(z)\tilde{W}_0(z) = H_1(z)\tilde{W}_1(z) = 1 \text{ if and only if } \tilde{\tau} = \tau_m, m \in \{0, 1\} \quad (20)$$

In the case of uncalibrated (noiseless) sensors, two deconvolvers tuned to hypothesized time-constants may be applied to the sensor current signals, yielding:

$$\tilde{J}_m[k] = \alpha_m \tilde{g}_{b,m} + \beta_m \quad (26)$$

where it may be observed that the baseline is unaltered by the deconvolver due to the fact that it has unit gain at zero frequency (constant) inputs because $\tilde{W}_m(z=1) = 1$. The sample Pearson correlation coefficient formed from the pair of deconvolver outputs may be written:

$$\tilde{r}(\tilde{\tau}_0, \tilde{\tau}_1) = \sum_{k=0}^{K-1} \tilde{\mathcal{J}}_0[k] \tilde{\mathcal{J}}_1[k] \quad (27)$$

where $$\tilde{\mathcal{J}}_m[k] = \frac{\tilde{J}_m[k] - \hat{\mu}_m}{\sqrt{\frac{1}{K-1} \sum_{k=0}^{K-1} (\tilde{J}_m[k] - \hat{\mu}_m)^2}}$$

and $$\hat{\mu}_m = \frac{1}{K} \sum_{k=0}^{K-1} \tilde{J}_m[k].$$

The following conjecture, which states that the correlation coefficient of the deconvolver outputs will be high if the hypothesized time-constants are correct, may then be made:

For hypothesized time-constants $\tilde{\tau}_m \in \mathcal{T}_{tm}$, $$\tilde{r}(\tilde{\tau}_0, \tilde{\tau}_1) = 1 \text{ if and only if } \tilde{\tau}_m = \tau_m, m \in \{0, 1\}. \quad (28)$$

When noise is present, the deconvolver transfer function may be adjusted to prevent high-frequency noise amplification. This may involve cascading the original high-pass deconvolver of Equation 19 with a low-pass filter:

$$\tilde{W}_m(z) \rightarrow \tilde{W}_m(z) LPF(z) \quad (29)$$

where LPF(z) is the transfer function of an appropriately designed low-pass filter.

Under the assumption of full sensor calibration, the time-constants may be estimated as:

$$\hat{\tau}_0, \hat{\tau}_1 = \underset{\tilde{\tau}_0, \tilde{\tau}_1}{\operatorname{argmin}} L(\tilde{\tau}_0, \tilde{\tau}_1) \quad (30)$$

where $$L(\tilde{\tau}_0, \tilde{\tau}_1) = \sqrt{\frac{1}{K} \sum_{k=0}^{K-1} (\tilde{g}_{b,0}[k] - \tilde{g}_{b,1}[k])^2} \quad (31)$$

The identifiability theorem may mean that for perfectly calibrated sensors, both the first time-constant and the second time-constant may be estimated by testing different hypothesized time-constants. For each hypothesized first time-constant $\tilde{\tau}_0$, an estimated blood glucose history $\tilde{g}_{b,0}[k]$ may be generated by deconvolving the history of first sensor measurements $\tilde{g}_{b,1}[k]$ with a deconvolver based on the hypothesized first time-constant. Similarly, for each hypothesized second time-constant $\tilde{\tau}_1$, an estimated blood glucose history $\tilde{g}_{b,1}[k]$ may be generated by deconvolving the history of second sensor measurements $\tilde{g}_{i,1}[k]$ with a deconvolver based on the hypothesized second time-constant. Then, a pair of hypothesized time-constants $\tilde{\tau}_0$, $\tilde{\tau}_1$ that minimizes a measure of the difference $\tilde{g}_{b,0}[k] - \tilde{g}_{b,1}[k]$ may be selected as the estimated in-vivo time-constants of the sensors. For imperfectly calibrated sensors (for which only approximate calibration parameters are available) the same approach may be used, to similar effect. For uncalibrated sensors, deconvolved measured sensor currents may be used to test hypothesized time constants, using the Pearson correlation coefficient as a measure of the difference between the deconvolved signals. In some embodiments, if the difference between the time-constants $\tilde{\tau}_0$, $\tilde{\tau}_1$ is too small to allow the time constants to be reliably estimated, the system may alert the subject or the clinician.

In some embodiments, the technique for estimating time constants may be used in combination with comparator data (data, such as finger stick data, that are more accurate or that exhibit lower time constants than the raw data from the sensors being calibrated). Combining the estimating techniques disclosed herein with comparator data may (i) reduce the amount of comparator data needed to jointly estimate sensor calibration parameters together with the diffusion time constants or (ii) improve the quality of the parameter estimates.

The measure of the difference may be any suitable function the value of which is greater the greater the extent to which the two estimated blood glucose histories differ. As such, the measure of the difference may be for example, the RMSE, the mean squared error (MSE), the average difference, the average relative difference, or the median of the average differences. As used herein, a measure of the difference between two signals may be minimized by (i) minimizing a measure of the difference between the signals, or by (ii) maximizing a measure of the similarity (e.g., the Pearson correlation coefficient) of the two signals. As used herein, a "sensor measurement" may be a direct measurement of a physical signal from a sensor (e.g., a measurement of a sensor current or of a corresponding voltage), or it may be a calculated signal, e.g., a calibrated sensor measurement (which may be an estimate of interstitial blood glucose). In some embodiments three or more sensors may be used, and pairs of time constants may be estimated from any pair of such sensors.

In some embodiments other methods for evaluating hypothesized time-constants may be employed. For example, one or both of (i) the history of first sensor measurements and (ii) the history of second sensor measurements may be filtered with one or more additional common filters and a measure of the difference between the filtered outputs may be used to determine the time constants. If, for example, the inverse of a deconvolver is used as a common additional filter, then one of the histories of sensor measurements may be left unfiltered.

In general, a first signal history may be calculated based on one or both sensor measurement histories and one or both hypothesized time-constants, and a second signal history may be calculated based on one or both sensor measurement histories and one or both hypothesized time-constants, and the values of the hypothesized time-constants that minimize a measure of the difference between the first signal history and the second signal history may be found. As used herein, a "signal history" is a set of values that a signal (e.g., a physical signal, such as a sensor current, or a derived signal, such as an interstitial glucose measurement based on the sensor current) takes at a set of points in time.

In practice, the testing of the hypothesized time-constants may be performed in parallel; e.g., a finite bank of deconvolvers tuned to different time-constants for each of the sensors may be used to approximate Equation 30. For a first sensor and a second sensor, for example, a measure of the difference may then be calculated for each pair of (i) an output history of a deconvolver of the bank of deconvolvers of the first sensor and (ii) an output history of a deconvolver of the bank of deconvolvers of the second sensor, and the pair of time-constants for which the measure of the difference is least may be identified.

The sampling of the sensors may be synchronized or unsynchronized. To the extent that it is unsynchronized, differences between samples that are near each other in time may be used, if the sampling rate is much greater than the reciprocal of the time-constants being estimated, or interpolation may be used.

For uncalibrated sensors, the time-constants may be estimated as:

$$\tilde{\tau}_0, \tilde{\tau}_1 = \arg\max_{\tilde{\tau}_0, \tilde{\tau}_1} \tilde{r}(\tilde{\tau}_0, \tilde{\tau}_1) \quad (32)$$

Under the assumption of calibrated sensors, if the interstitial glucose measurement noise associated with one sensor is not perfectly correlated with that of the other sensor, an improved blood glucose estimate may be obtained by forming a (possibly weighted) average of the two individual blood glucose estimates obtained from deconvolvers tuned to the estimated time-constants:

$$\hat{g}_b[k] = c_0 \hat{g}_{b,0}[k] + c_1 \hat{g}_{b,1}[k] \quad (33)$$

where $c_m \geq 0$ are the weights, and $\hat{g}_{b,m}[k]$ are the individual blood glucose estimates at the estimated time-constants.

Figure 4:
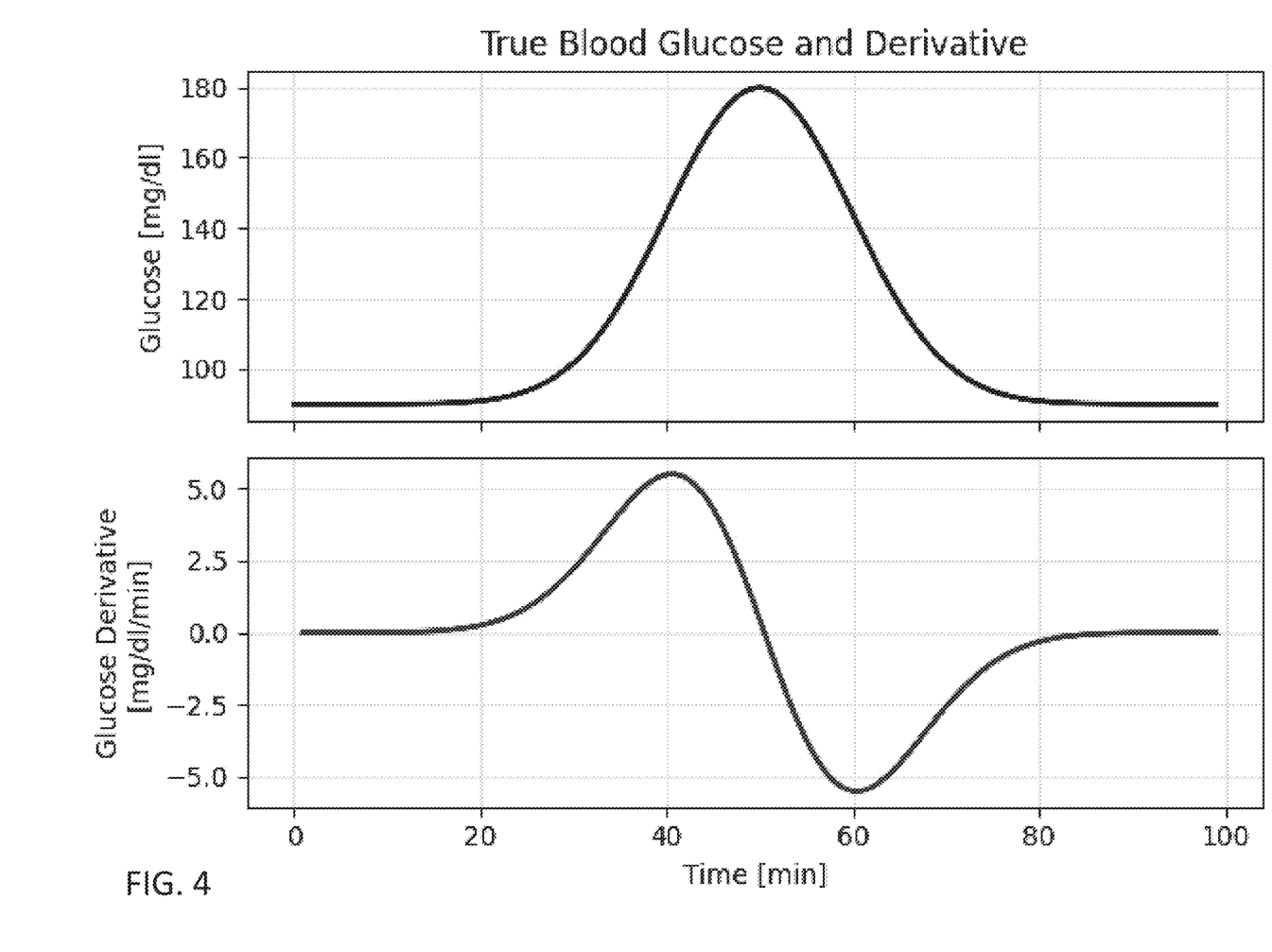
FIG. 4 is a graph of a blood glucose peak, together with its derivative, according to an embodiment of the present disclosure.

As mentioned above, numerical simulations were performed to support the conclusions arrived at above. For the simulations, the computer-synthesized blood glucose peak shown, together with its derivative, in FIG. 4, was used. The time-constants associated with the simulated shallow and deep sensors were $\tau_0=3$ minutes and $\tau_1=12$ minutes respectively. Deconvolver banks were centered at the true time-constants spanning ±3 min in one-minute increments.

For calibrated sensors, the simulated cost function of $L(\tilde{\tau},\tilde{\tau})$ of Equation 31 (which may also be referred to as the root mean squared error (RMSE)) is shown in FIGS. 2A and 2B. It may be seen that the RMSE is lowest at the correct pair of hypothesized time-constants: $\tilde{\tau}_0=\tau_0$ and $\tilde{\tau}_1=\tau_1$.

Figure 5:
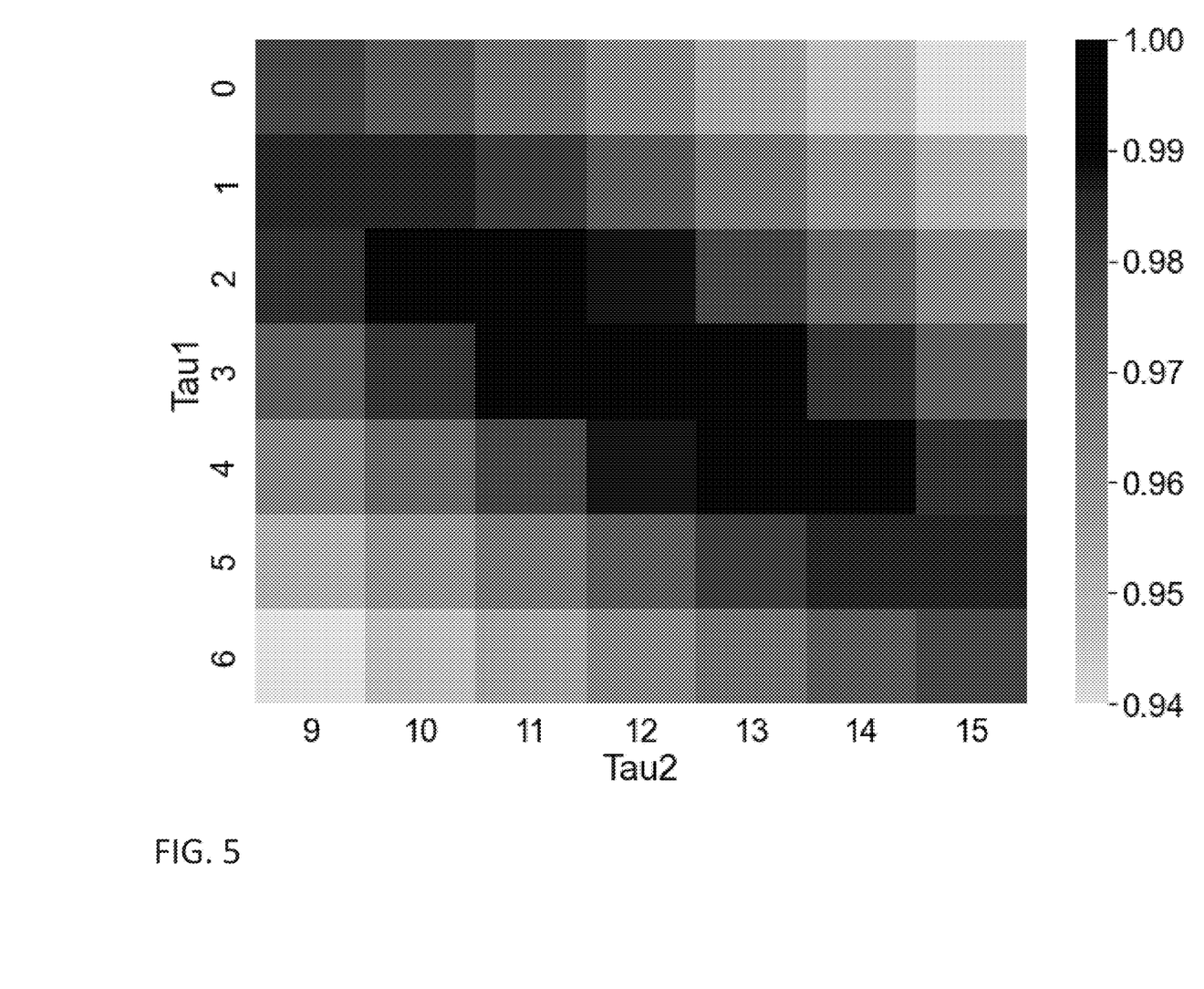
FIG. 5 is a graph of a simulated Pearson correlation coefficient, according to an embodiment of the present disclosure.
Figure 6:
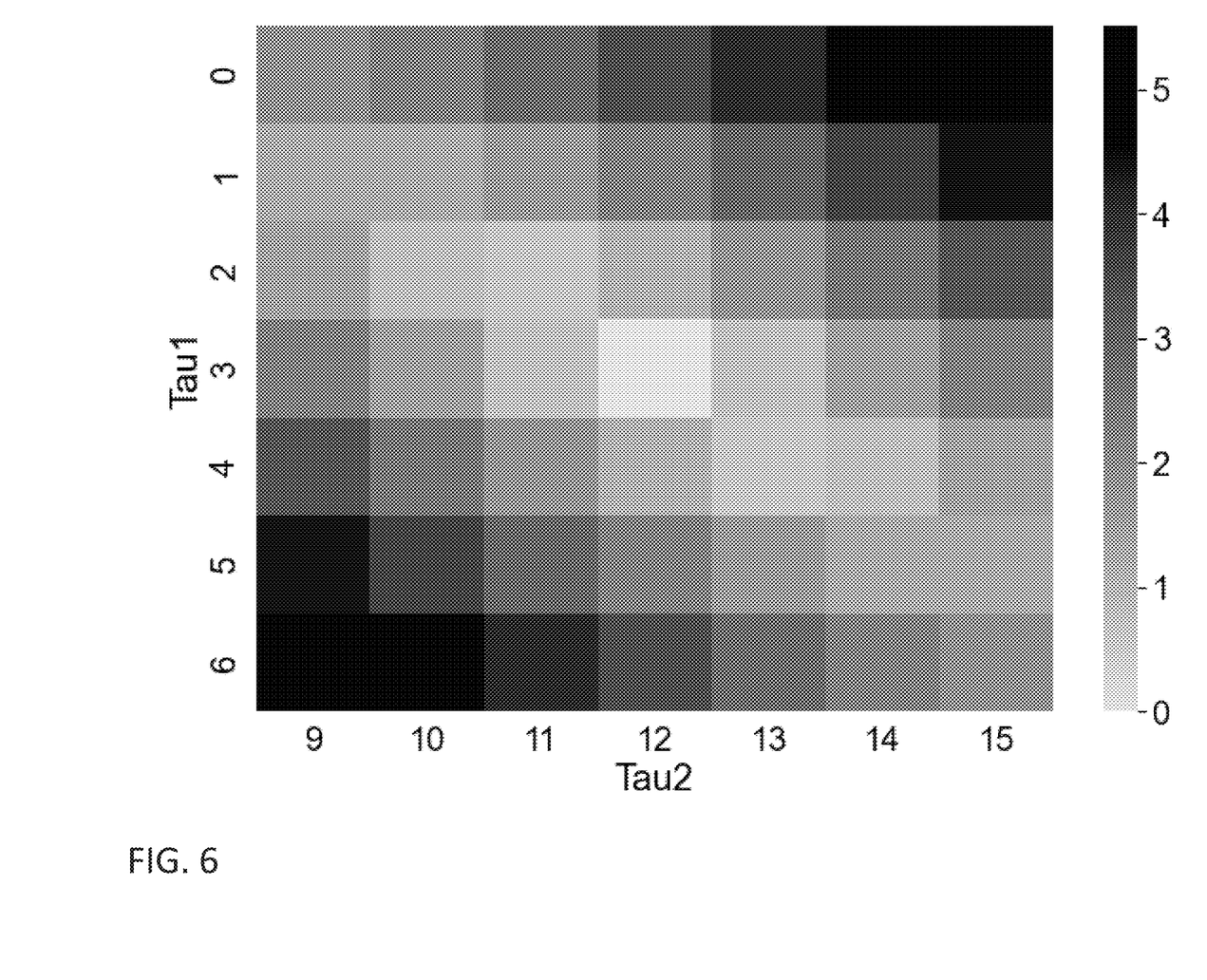
FIG. 6 is a graph of a mean absolute relative difference, according to an embodiment of the present disclosure.

For uncalibrated sensors, the simulated Pearson correlation coefficient is shown in FIG. 5, (with the hypothesized time-constant of the first sensor ("Tau1") on the vertical axis and the hypothesized time-constant of the second sensor ("Tau2") on the horizontal axis). It may be seen from FIGS. 2A and 5 that both the RMSE (for calibrated sensors) and the Pearson correlation coefficient (for uncalibrated sensors) are significantly more sensitive to the difference $\tilde{\tau}_1-\tilde{\tau}_0$ between the hypothesized time-constants than to their sum or average. As such, these measures of the difference between signal histories may be used to estimate the time constant of one sensor when the time constant of another sensor is known (e.g., as a result of a calibration, or if the other sensor is a series of finger sticks). The mean absolute relative difference (MARD), defined as:

$$MARD [\%] = \frac{100}{K} \Sigma_{k=0}^{K-1} \left| \frac{\hat{g}_b[k] - g_b[k]}{g_b[k]} \right|$$

is shown in FIG. 6 (with the hypothesized time-constant of the first sensor ("Tau1") on the vertical axis and the hypothesized time-constant of the second sensor ("Tau2") on the horizontal axis) for the average of the two deconvolver outputs. As expected, MARD is minimized at the true time-constants.

In some embodiments, instead of using a bank of deconvolvers to estimate the blood glucose, a bank of deconvolvers each estimating a function of the blood glucose, e.g., the derivative, with respect to time, of the blood glucose, is employed. As used herein, "estimating the blood glucose level" includes estimating any quantity that depends on the blood glucose level, e.g., the derivative of the blood glucose level.

As used herein, an "in-vivo calibration parameter" for a sensor is an attribute of the sensor's response to blood glucose, when the sensor is implanted in the patient. As such, in-vivo calibration parameters include the sensitivity and background current of the sensor, as well as the time-constants (or "in-vivo time-constants") relating blood glucose to the interstitial fluid at the point of implantation of the sensor.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X−Y and the second quantity is at most X+Y. As used herein, when a second number is "within Y %" of a first number, it means that the second number is at least (1−Y/100) times the first number and the second number is at most (1+Y/100) times the first number. As used herein, the word "or" is inclusive, so that, for example, "A or B" means any one of (i) A, (ii) B, and (iii) A and B.

The methods described herein may be performed by a processing circuit. The term "processing circuit" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

As used herein, when a method (e.g., an adjustment) or a first quantity (e.g., a first variable) is referred to as being "based on" a second quantity (e.g., a second variable) it means that the second quantity is an input to the method or influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory as) the second quantity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed herein could be termed a second element, component, region, layer or section, without departing from the spirit and scope of the inventive concept.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

As used herein, the singular forms "a" and "an" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the inventive concept refers to "one or more embodiments of the present disclosure". Also, the term "exemplary" is intended to refer to an example or illustration. As used herein, the terms "use," "using," and "used" may be considered synonymous with the terms "utilize," "utilizing," and "utilized," respectively.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., (1−35/100) times 10) and the recited maximum value of 13.5 (i.e., (1+35/100) times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although exemplary embodiments of a personalized calibration method for glucose sensing have been specifically described and illustrated herein, many modifications and variations will be apparent to those skilled in the art. Accordingly, it is to be understood that a personalized calibration method for glucose sensing constructed according to principles of this disclosure may be embodied other than as specifically described herein. The invention is also defined in the following claims, and equivalents thereof.

What is claimed is:

1. A method, comprising:
obtaining a plurality of first glucose measurements from a subject, at a plurality of first sampling times during a time interval, using a first glucose sensor;
obtaining a plurality of second glucose measurements from the subject, at a plurality of second sampling times during the time interval, using a second glucose sensor;
calculating a plurality of first signal histories and a plurality of second signal histories;
estimating a first in-vivo time-constant for the first glucose sensor and a second in-vivo time-constant, different from the first in-vivo time constant, for the second glucose sensor, based on the first glucose measurements and the second glucose measurements; and
converting a glucose measurement of the first glucose sensor to a calibrated glucose measurement,
wherein:
an output of the first glucose sensor is related to a change in a blood glucose concentration by a first low-pass filter response, the first low-pass filter response being characterized by the first in-vivo time-constant,
an output of the second glucose sensor is related to a change in a blood glucose concentration by a second low-pass filter response, the second low-pass filter response being characterized by the second in-vivo time-constant,
the estimating comprises selecting a first time-constant and a second time-constant for which a measure of the difference between a first signal history, of the first signal histories, and a second signal history of the second signal histories is minimized,
each of the first signal history and the second signal history is based on the first glucose measurements or the second glucose measurements or a first hypothesized time-constant or a second hypothesized time-constant,
the calculating of each of the first signal histories comprises deconvolving the first glucose measurements with a respective deconvolver of a set of deconvolvers each tuned to a respective one of a plurality of hypothesized time-constants including the first hypothesized time-constant, and
the calculating of each of the second signal histories comprises deconvolving the second glucose measurements with a respective deconvolver of a set of deconvolvers each tuned to a respective one of a plurality of hypothesized time-constants including the second hypothesized time-constant.

2. The method of claim 1, further comprising estimating a blood glucose level based on:
a glucose measurement from the first glucose sensor; and
the estimated first in-vivo time-constant.

3. The method of claim 1, further comprising estimating a blood glucose level based on:
a glucose measurement from the first glucose sensor;

a glucose measurement from the second glucose sensor;
the estimated first in-vivo time-constant; and
the estimated second in-vivo time-constant.

4. The method of claim 1, wherein:
the measure of the difference between the first signal history and the second signal history is a measure of the difference between an estimated blood glucose history based on the first glucose measurements and an estimated blood glucose history based on the second glucose measurements; and
the measure of the difference between the estimated blood glucose history based on the first glucose measurements and the estimated blood glucose history based on the second glucose measurements is selected from the group consisting of a root mean square error, a mean squared error, an average difference, an average relative difference, and the median of average differences.

5. The method of claim 4, wherein the measure of the difference between the estimated blood glucose history based on the first glucose measurements and the estimated blood glucose history based on the second glucose measurements is a root mean square error.

6. The method of claim 1, comprising estimating the difference between the first in-vivo time-constant and the second in-vivo time-constant.

7. The method of claim 1, wherein:
the first glucose sensor is in a deep subcutaneous space of the subject; and
the second glucose sensor is in a shallow dermis of the subject.

8. A system, comprising:
a processing circuit; and
memory, operatively connected to the processing circuit and storing instructions that, when executed by the processing circuit, cause the system to perform a method, the method comprising:
obtaining a plurality of first glucose measurements from a subject, at a plurality of first sampling times during a time interval, using a first glucose sensor;
obtaining a plurality of second glucose measurements from the subject, at a plurality of second sampling times during the time interval, using a second glucose sensor;
calculating a plurality of first signal histories and a plurality of second signal histories; and
estimating a first in-vivo time-constant for the first glucose sensor and a second in-vivo time-constant, different from the first in-vivo time constant, for the second glucose sensor, based on the first glucose measurements and the second glucose measurements,
wherein:
an output of the first glucose sensor is related to a change in a blood glucose concentration by a first low-pass filter response, the first low-pass filter response being characterized by the first in-vivo time-constant,
an output of the second glucose sensor is related to a change in a blood glucose concentration by a second low-pass filter response, the second low-pass filter response being characterized by the second in-vivo time-constant,
the estimating comprises selecting a first time-constant and a second time-constant for which a measure of the difference between a first signal history, of the first signal histories, and a second signal history, of the second signal histories, is minimized,
each of the first signal history and the second signal history is based on the first glucose measurements or the second glucose measurements or a first hypothesized time-constant or a second hypothesized time-constant,
the calculating of each of the first signal histories comprises deconvolving the first glucose measurements with a respective deconvolver of a set of deconvolvers each tuned to a respective one of a plurality of hypothesized time-constants including the first hypothesized time-constant, and
the calculating of each of the second signal histories comprises deconvolving the second glucose measurements with a respective deconvolver of a set of deconvolvers each tuned to a respective one of a plurality of hypothesized time-constants including the second hypothesized time-constant.

9. The system of claim 8, wherein the method further comprises estimating a blood glucose level based on:
a glucose measurement from the first glucose sensor; and
the estimated first in-vivo time-constant.

10. The system of claim 8, wherein the method further comprises estimating a blood glucose level based on:
a glucose measurement from the first glucose sensor;
a glucose measurement from the second glucose sensor;
the estimated first in-vivo time-constant; and
the estimated second in-vivo time-constant.

11. The system of claim 8, wherein:
the measure of the difference between the first signal history and the second signal history is a measure of the difference between an estimated blood glucose history based on the first glucose measurements and an estimated blood glucose history based on the second glucose measurements; and
the measure of the difference between the estimated blood glucose history based on the first glucose measurements and the estimated blood glucose history based on the second glucose measurements is selected from the group consisting of a root mean square error, a mean squared error, an average difference, an average relative difference, and the median of average differences.

12. The system of claim 8, wherein the method further comprises estimating the difference between the first in-vivo time-constant and the second in-vivo time-constant.

13. The system of claim 8, wherein the obtaining of the first glucose measurements comprises obtaining the first glucose measurements using an electro-chemical sensor of a continuous glucose monitor.

* * * * *